United States Patent [19]
Tsuchii et al.

[11] Patent Number: 5,854,058
[45] Date of Patent: Dec. 29, 1998

[54] METHOD OF DECOMPOSING HARD TYPE RUBBER PRODUCTS

[75] Inventors: Akio Tsuchii, Ibaraki; Kiyoshi Takeda, Aomori; Yutaka Tokiwa, Ibaraki, all of Japan

[73] Assignee: Director-General of Agency of Industrial Science and Technology, Tokyo, Japan

[21] Appl. No.: 789,331

[22] Filed: Jan. 23, 1997

[30] Foreign Application Priority Data

Jan. 23, 1996 [JP] Japan .................................. 8-008807

[51] Int. Cl.⁶ ...................................................... C12S 13/00
[52] U.S. Cl. .................. 435/262; 435/262.5; 435/253.2; 435/872
[58] Field of Search ................................ 435/253.2, 262, 435/262.5, 267, 872

[56] References Cited

U.S. PATENT DOCUMENTS 5,043,035  8/1991  Yoshikawa ............................... 435/872

FOREIGN PATENT DOCUMENTS 60-072934  4/1985  Japan .
61-085193  4/1986  Japan .
2-076575  3/1990  Japan .

OTHER PUBLICATIONS

Heisey et al. "Isolation of Microoragnisms Able to Metabolize Purified Natural Rubber." Applied and Environmental Microbiology. vol. 61, No. 8 (Aug. 1995), pp. 3092–3097.

Tsuchii et al. "Microbial Degradation of Natural Rubber Vulcanizates." Applied and Environmental Microbiology. vol. 50, No. 4 (Oct. 1985), pp. 965–670.

Tsuchii et al. "The Effect of Compounding Ingredients on Microbial Degradation of Vulcanized Natural Rubber." Journal of Applied Polymer Science. vol. 41 (1990), pp. 1181–1187.

*Primary Examiner*—William H. Beisner
*Attorney, Agent, or Firm*—Fish & Richardson, P.C.

[57] ABSTRACT

The present invention relates to a method of decomposing hard type rubber products, which comprises treating hard type rubber products with a microorganism belonging to the genus Nocardia in the presence of soft type rubber products. According to the present invention, hard type rubber products, particularly tires, can be efficiently decomposed.

1 Claim, No Drawings

METHOD OF DECOMPOSING HARD TYPE RUBBER PRODUCTS

FIELD OF THE INVENTION

The present invention relates to a method of decomposing hard type rubber products.

BACKGROUND OF THE INVENTION

Generally, waste rubber products are disposed of by combustion or landfill mainly, and similarly to plastics there are problems including damage to a furnace at high temperature and there is a need for development of an advanced technology. Many proposals have been made for the technology for the disposal, reclamation or recycling of waste tires and are practically used. However, these disposal methods suffer from problems in technical factors such as secondary pollution caused by reuse of waste tires or requirement for much energy and are further affected greatly by economical factors such as costs for collection and transport of waste tires or fluctuations of the petroleum price. Hence, a great amount of annually generated waste tires as well as the disposal of waste plastics, etc., are still regarded as the cause of serious environmental pollution.

Therefore, a disposal method, if established with high efficiency using a microorganism, would be considered useful as pollution-free and energy-saving technology utilizing substance circulation in a natural ecological system.

Under these circumstances, the present inventors reported a batch or semi-continuous method by use of a microorganism as a method of decomposing natural rubber on the basis of the knowledge that soft type natural rubber products can be easily decomposed and used as a growth substrate by rubber-decomposing microorganisms (Japanese Patent Publication Nos. 60634/1992 and 5426/1988).

However, these methods are directed to soft type rubber products and cannot be applied to hard type rubber products such as tires which are hardly decomposed by rubber-decomposing microorganisms.

Therefore, there is a need for development of a method capable of decomposing such hard type rubber products.

SUMMARY OF THE INVENTION

The object of the present invention is to provide a method of decomposing hard type rubber products by use of microorganisms.

As a result of their eager research, the present inventors found that hard type rubber products can be decomposed by treatment thereof with a microorganism belonging to the genus Nocardia in the presence of soft type rubber products.

That is, the present invention is a method of decomposing hard type rubber products, which comprises treating hard type rubber products with a microorganism belonging to the genus Nocardia in the presence of soft type rubber products.

The microorganism belonging to the genus Nocardia includes Nocardia NR-35A. The hard type rubber products include tires.

DETAILED DESCRIPTION OF THE INVENTION

Hereinafter, the present invention is described in detail.

The method of decomposing hard type rubber according to the present invention is characterized by treatment (i.e. decomposition reaction under predetermined conditions) of hard type rubber products as the subject of decomposition with a microorganism belonging to the genus Nocardia in the presence of soft type rubber products.

Nocardia NR-35A can be used as the microorganism belonging to the genus Nocardia. Nocardia NR-35A was deposited on Jan. 9, 1997 as FERM BP-5784 with the National Institute of Bioscience and Human-Technology, Agency of Industrial Science and Technology, Japan.

The most important feature in the present invention is that the decomposition reaction of hard type rubber is carried out in the presence of soft type rubber products which are relatively well decomposed and utilized as a growth substrate by rubber-decomposing microorganisms. The soft type rubber products include natural or synthetic isoprene-based rubber products, such as commercial rubber gloves, rubber bands, etc. The hard type rubber products include tires etc.

For the decomposition reaction, conditions in accordance with methods of culturing conventional aerobic microorganisms can be adopted. For example, the medium is that containing inorganic salts such as salts of nitrogen, phosphorus, etc. in addition to rubber serving as the substrate for the microorganism used in the present invention. The reaction temperature is 20° to 37° C., preferably 30° C., and the pH is 6.0 to 8.0, preferably pH 7.

First, the rubber-decomposing microorganism is cultured with a soft type rubber to prepare a stock inocula.

In this case, a soft type rubber product is cut into pieces of 20 to 120 mm in size and mixed in an amount of 50 to 100 mg/100 ml in a reactor. The rubber-decomposing microorganism is mixed at a density of $10^7$ to $10^{10}$ cells/100 ml.

Separately, a hard type rubber product is cut into pieces of 20 or less to 120 mm in size and mixed in an amount of 10 to 50 mg/100 ml to prepare a hard type rubber-containing medium.

To this hard type rubber-containing medium are then added a soft type rubber product in a suitable amount and an inoculum in an amount of 1 to 10 ml ($10^7$ to $10^{10}$ cells) every 100 ml of the hard type rubber-containing medium. The microorganism is then cultured at 20 to 37° C. for 28 to 56 days or more.

Under these reaction conditions, the decomposition of the hard type rubber (tire) is significantly accelerated and 50% or more is decomposed in 8-week decomposition reaction. In this decomposition, a part of natural rubber contained in the tire is completely decomposed as a growth substrate by the rubber-decomposing microorganism while a part of the rubber is recovered as fine rubber particles of 30 $\mu$m or less in diameter.

The rate and degree of decomposition of tire rubber vary depending on the type and part of tire, and generally, products using a large amount of natural rubber as elastomeric materials are well decomposed. Therefore, large tires for trucks and buses using relatively large amounts of natural rubber, particularly steel radial type products, are suitable for their disposal by decomposition in the method of the present invention.

According to the present invention, hard type rubber products, particularly tires with a high content of natural rubber, can be effectively decomposed and rubber particles as fine as about 3 to 30 $\mu$m can be recovered.

EXAMPLES

Hereinafter, the present invention is described in more detail by Examples, which however are not intended to limit the scope of the present invention.

Example 1

0.2 g piece cut from a commercial rubber glove was added to 200 ml medium with the composition shown in Table 1, and Nocardia NR-35A (FERM BP-5784) was inoculated using one loop of platinum into the medium and cultured at 30° C., pH 7 for 20 days, and the resulting culture was used as a stock microorganism.

Separately, 30 mg piece of rubber from a large tire tread for trucks and buses was added to 100 ml medium (in 300-ml Erlenmeyer flask) with the composition shown in Table 1 to prepare a hard type rubber-containing medium.

TABLE 1

| | |
|---|---|
| $(NH_4)_2SO_4$ | 2.0 g |
| $KH_2PO_4$ | 0.2 g |
| $K_2HPO_4$ | 1.6 g |
| $MgSO_4.7H_2O$ | 0.1 g |
| NaCl | 0.1 g |
| $CaCl_2.2H_2O$ | 0.01 g |
| $FeSO_4$ | 5 mg |
| $Na_2MoO_4.2H_2O$ | 0.5 mg |
| $Na_2WO_4.2H_2O$ | 0.5 mg |
| $MnSO_4$ | 0.5 mg |
| distilled water | 1000 ml |
| pH | 7.5 |

Then, said stock microorganism was added to said hard type rubber-containing medium and the decomposition reaction was carried out at 30° C. under stirring with a magnetic stirrer. After the 56-day decomposition reaction, a piece of tire rubber was removed and boiled for 10 minutes in 1N NaOH. After this alkali treatment, the piece of tire rubber was washed sufficiently with water and vacuum-dried, and the reduction in weight was determined.

The control was subjected to the same decomposition reaction except that soft type rubber was not added.

The result indicated that the reduction in weight was 13% in the reaction in the absence of soft type rubber, while the reduction in weight was 51% in the reaction in the presence of 70 mg piece of rubber cut from a commercial rubber glove. Further, a large number of fine particles (diameter of 100 μm or less, predominantly 3 to 30 μm) were contained in the culture as well as in the wash obtained by washing the piece of rubber after the alkali treatment. The weight of the fine particles of rubber corresponded to 28% of the piece of tire rubber.

Example 2

Four kinds of tire tread were decomposed under the same conditions as in Example 1.

The starting rubber was analyzed for its composition (content of natural rubber) by pyrolysis gas chromatography.

The results are shown in Table 2. As can be seen from Table 2, the radial tire with a higher content of natural rubber was effectively decomposed by the method of the present invention.

TABLE 2

| Type of tire | After alkali treatment reduction in weight in presence of glove rubber | Content of natural rubber |
|---|---|---|
| Biasply tire A | 20 ± 6% | 65 phr* |
| Biasply tire B | 3 ± 1% | 55 phr |
| Radial tire A | 40 ± 3% | 70 phr |
| Radial tire B | 35 ± 1% | 100 phr |

*phr: parts per handred rubbber

Example 3

Rubber from various parts of a large tire for tracks (see Table 3) was decomposed under the same conditions as in Example 1. The content of natural rubber was analyzed using the same means as in Example 2.

The results are shown in Table 3. As can be seen from Table 3, the tread cap and side wall were sufficiently decomposed.

TABLE 3

| Site of tire | After alkali treatment reduction in weight in presence of glove rubber | Content of natural rubber |
|---|---|---|
| Tread cap | 55 ± 3% | 100 phr |
| Base tread | 14 ± 1% | 100 phr |
| Side wall | 35 ± 2% | 30 phr |
| Inner liner | 5 ± 2% | 65 phr |
| Bead | 0 ± 1% | 100 phr |

What is claimed is:

1. A method of decomposing tires, which comprises contacting tires with a culture of Nocardia NR-35A in the presence of a natural or synthetic isoprene-based rubber product.

* * * * *